(12) United States Patent
Meergans et al.

(10) Patent No.: US 9,339,550 B2
(45) Date of Patent: *May 17, 2016

(54) SOLID IVABRADINE-CONTAINING COMPOSITION

(71) Applicant: ratiopharm GmbH, Ulm (DE)

(72) Inventors: Dominique Meergans, Munich (DE); Daniela Stumm, Berlin (DE); Jens Geier, Hayingen (DE)

(73) Assignee: ratiopharm GmbH, Ulm (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/517,015

(22) Filed: Oct. 17, 2014

(65) Prior Publication Data

US 2015/0038491 A1 Feb. 5, 2015

Related U.S. Application Data

(63) Continuation of application No. 13/704,580, filed as application No. PCT/EP2011/059866 on Jun. 14, 2011, now Pat. No. 8,900,605.

(30) Foreign Application Priority Data

Jun. 14, 2010 (EP) .................................... 10165881
Jun. 14, 2010 (EP) .................................... 10165884
Jun. 23, 2010 (IN) ........................... 1760/CHE/2010

(51) Int. Cl.

| A61K 9/20 | (2006.01) |
|---|---|
| A61K 47/10 | (2006.01) |
| A61K 47/36 | (2006.01) |
| A61K 47/32 | (2006.01) |
| A61K 47/38 | (2006.01) |
| A61K 31/55 | (2006.01) |
| A61K 9/28 | (2006.01) |
| C07D 223/16 | (2006.01) |
| A61K 9/14 | (2006.01) |
| A61K 9/00 | (2006.01) |
| C07C 55/14 | (2006.01) |
| A61K 9/16 | (2006.01) |

(52) U.S. Cl.
CPC ............... *A61K 47/38* (2013.01); *A61K 9/0002* (2013.01); *A61K 9/14* (2013.01); *A61K 9/146* (2013.01); *A61K 9/1652* (2013.01); *A61K 9/20* (2013.01); *A61K 9/2027* (2013.01); *A61K 9/2031* (2013.01); *A61K 9/2054* (2013.01); *A61K 9/2095* (2013.01); *A61K 9/2846* (2013.01); *A61K 31/55* (2013.01); *A61K 47/10* (2013.01); *A61K 47/32* (2013.01); *A61K 47/36* (2013.01); *C07C 55/14* (2013.01); *C07D 223/16* (2013.01); *Y10T 428/2982* (2015.01)

(58) Field of Classification Search
CPC . A61K 31/55; A61K 31/472; A61K 49/0002; A61K 9/146; A61K 9/1635; A61K 9/1694; A61K 9/2027; A61K 9/2031; A61K 9/2095
See application file for complete search history.

(56) References Cited

U.S. PATENT DOCUMENTS

| 7,014,866 B2 | 3/2006 | Infeld |
| 2004/0028743 A1 | 2/2004 | Wuthrich et al. |
| 2010/0119459 A1 | 5/2010 | Lerebours-Pigeonniere |

FOREIGN PATENT DOCUMENTS

| DE | 601 26 332 T2 | 8/2007 |
| WO | WO2009/124940 A1 * | 10/2009 |
| WO | WO 2009/158005 A1 | 12/2009 |

OTHER PUBLICATIONS

Sameer Singh et al., "A Review on Solid Dispersion", International Journal of Pharmacy and Life Sciences, Sep. 2011, vol. 2, Issue No. 9, pp. 1078-1095.

* cited by examiner

*Primary Examiner* — Audrea Buckley
(74) *Attorney, Agent, or Firm* — Chalin A. Smith; Smith Patent

(57) ABSTRACT

The present invention relates to a solid composition containing ivabradine or a pharmaceutically acceptable salt thereof. Further, the invention relates to a method for the preparation of such a composition as well as a pharmaceutical product comprising such a composition.

12 Claims, 6 Drawing Sheets

SOLID IVABRADINE-CONTAINING COMPOSITION

PRIORITY

This application is a continuation of U.S. Ser. No. 13/704,580 filed Feb. 4, 2013, which, in turn, corresponds to the U.S. national phase of International Application No. PCT/EP2011/059866 filed Jun. 14, 2011, which, in turn, claims priority to European Patent Application No. 10.165881.3 filed Jun. 14, 2010, European Patent Application No. 10.165884.7 filed Jun. 14, 2010, and Indian Patent Application No. 1760/CHE/2010 filed Jun. 23, 2010, the contents of which are incorporated by reference herein in their entirety.

FIELD OF THE PRESENT INVENTION

The present invention relates to a solid composition containing ivabradine or a pharmaceutically acceptable salt thereof. The invention further relates to a method for the preparation of such a composition as well as a pharmaceutical product comprising such a composition.

BACKGROUND OF THE PRESENT INVENTION

Ivabradine has the chemical designation (S)-3-{3-[(3,4-dimethoxybicyclo[4.2.0]octa-1,3,5-triene-7-ylmethyl)methylamino]propyl}-7,8-dimethoxy-2,3,4,5-tetrahydro-1H-3-benzazepine-2-one. Ivabradine has the following structural formula (I):

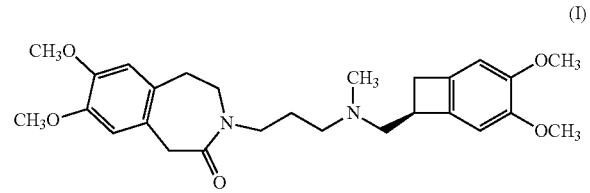

Synthesis routes for the preparation of ivabradine and its use for preventing and treating various clinical conditions of myocardial ischaemia, supraventricular arrhythmias and coronary arteriosclerotic episodes are reported to be disclosed in EP 534 859.

Ivabradine is an active substance reported to have a bradycardic effect for the treatment of stable angina pectoris, in particular in patients for whom beta-blockers are contraindicated or an intolerance of beta-blockers is present. Ivabradine is reported to selectively inhibit the $I_f$-ion current, which, as an intrinsic pacemaker in the heart, controls the spontaneous diastolic depolarisation in the sino-atrial node and thus regulates the heart rate. Under physiological conditions, ivabradine, the S-enantiomer of a racemate, is reported to have a very good solubility (>10 mg/ml).

The prior art apparently discloses administration forms of ivabradine, which release the active substance substantially without a time delay. The administration form Procoralan® (Servier), which is prepared by wet granulation, releases ivabradine rapidly and almost completely after oral intake. WO 2003-061662 apparently discloses an ivabradine-containing, orally dispersible tablet, which releases the active substance very rapidly in the mouth.

Also solid pharmaceutical compositions for the controlled release of ivabradine are reported to be known. WO 2002/051387 apparently describes such a composition comprising a thermoformable mixture of ivabradine and one or more polymers selected from the group of the polymethacrylates. This composition is reported to be obtainable by mixing the active substance with the polymer with lowering of the viscosity of said mixture under the action of heat and shear forces of a screw inside the cylinder and pressing out the molten mixture. However, the document does not disclose whether the active substance dissolves in the polymer in this preparation method. No indications are also given to a particular embodiment of the method that could lead to the dissolution of the active substance in the polymer.

Moreover, various polymorphic forms of the ivabradine hydrochloride are reported to be described in the state of the art. WO 2005/110993 A1 apparently discloses polymorph alpha, WO 2006/092493 A1 apparently discloses polymorph beta, WO 2006/092491 A1 apparently discloses polymorph beta d (dehydrated). In addition, polymorph gamma, polymorph gamma d, polymorph delta, and polymorph delta d are reported to be known in the art. In addition, WO2008/065681 apparently reports the so-called Form I of Ivabradine HCl. WO 2008/146308 A2 apparently discloses amorphous ivabradine.

Also various salts of ivabradine are apparently known in the art. WO 2008/146308 A2 apparently discloses ivabradine oxalate, WO 2009/124940 A1 apparently discloses ivabradine hydrobromide.

SUMMARY OF THE PRESENT INVENTION

The problem with the salts and polymorphs of the ivabradine, in particular the polymorphs of the hydrochloride, is that these salt forms are not sufficiently stable under all conditions. This, in turn can lead to problems in the processing as well as the storage and to undesired reactions with the excipients employed in the preparation of the pharmaceutical composition.

Thus, it is an object of the present invention to provide a pharmaceutical composition, which has no problems regarding the polymorphic form of the active substance.

A further problem with the ivabradine-containing pharmaceutical compositions is that the amount of active substance in the formulation to be administered is usually only small. This leads to problems in the preparation of the corresponding compositions due to possible variations in content that are for example conditional on separation tendencies of the active substances and excipients. Therefore, it is important that at first active substances and excipients can be mixed as homogenous as possible and corresponding mixtures do not separate again during further processing to the final formulation. An inhomogeneous distribution of the active substance can result in undesired side effects up to symptoms of poisoning. Also the bioavailability as well as the effectiveness of corresponding formulations may be affected adversely in an inhomogeneous distribution of the active substance. Accordingly, for example the USP prescribes for ensuring patient safety a Multi-Stage Content Uniformity test according to which the content of 10 individual tablets having a RSD must be ≤6% and no value may be outside of 75-125%. Moreover, the content of at least 9 of 10 tablets is in the range of 85-115%. The uniformity of the content of individually dosed pharmaceutical dosage form ("Content Uniformity") is determined in accordance to Ph. Eur. 6.0, section 2.9.6.

It has been shown that neither problems regarding the stability of the employed polymorphic form of the active substance nor problems regarding the homogeneous distribution of the active substance in the final formulation can be solved by simply mixing and compressing the constituents.

Thus, a further object of the present invention is to provide a pharmaceutical composition that ensures a distribution of the active substance in the final formulation that is as homogeneous as possible. At the same time, the composition should not have any problems also in its later storage regarding the polymorphic form of the active substance.

Now, it has surprisingly been found that the above-mentioned problems can be solved in that the active substance ivabradine is homogenously and molecularly disperse mixed with a pharmaceutically acceptable excipient.

Thus, the present invention relates to a solid composition containing at least a pharmaceutically acceptable excipient and ivabradine or a pharmaceutically acceptable salt thereof as active substance characterized in that excipient and active substance are present in a homogeneous, molecularly disperse mixture.

DETAILED DESCRIPTION OF THE PREFERRED EMBODIMENTS

Presently, by "active substance" ivabradine in the form of the free base or a pharmaceutically acceptable salt thereof is meant. A suitable pharmaceutically acceptable salt is for example the hydrochloride, the hydrobromide, the oxalate, the sulfate, the phosphate, the acetate, the propionate, however also salts of the ivabradine with propionic acid, maleic acid, fumaric acid, tartaric acid, nitric acid, benzoic acid, methanesulfonic acid, isethionic acid, benzenesulfonic acid, citric acid, toluenesulfonic acid, trifluoroacetic acid, and camphoric acid and also the lactate, pyruvate, malonate, succinate, glutarate, and ascorbate of the ivabradine. Further, the following salts can be employed: L-aspartate, glutamate, sorbate, acinotate, gluconate, hippurate, and salts of the ivabradine with ethanesulfonic acid, mandelic acid, adipic acid, or sulfamic acid. The salts of the ivabradine can be obtained in accordance to methods reported to be known in the art by reacting the free base of the ivabradine with the corresponding acid or by the presence of the corresponding acid in the synthesis of the ivabradine, as reported to be described for example in US 2005/0228177 A1. Preferred are ivabradine hydrochloride, hydrobromide, adipate and oxalate.

Preferably the pharmaceutical composition according to the present application is a stable pharmaceutical composition.

Ivabradine adipate can be obtained by adding adipic acid, e.g. about one equivalent, in a suitable solvent, such as ethanol, to a solution of ivabradine in a suitable solvent, such as dichloromethane. Crystalline ivabradine adipate product can be obtained by removal of the solvent, e.g. under vacuum at about 40° C. Crystalline ivabradine adipate can also be obtained by adding a solution of adipic acid in water to a solution of ivabradine in ethanol, and removal of the solvent.

The DSC thermogram of ivabradine adipate shows a peak at about 115° C. The melting point is in the range of about 113° C. to about 117° C.

Figure 1:
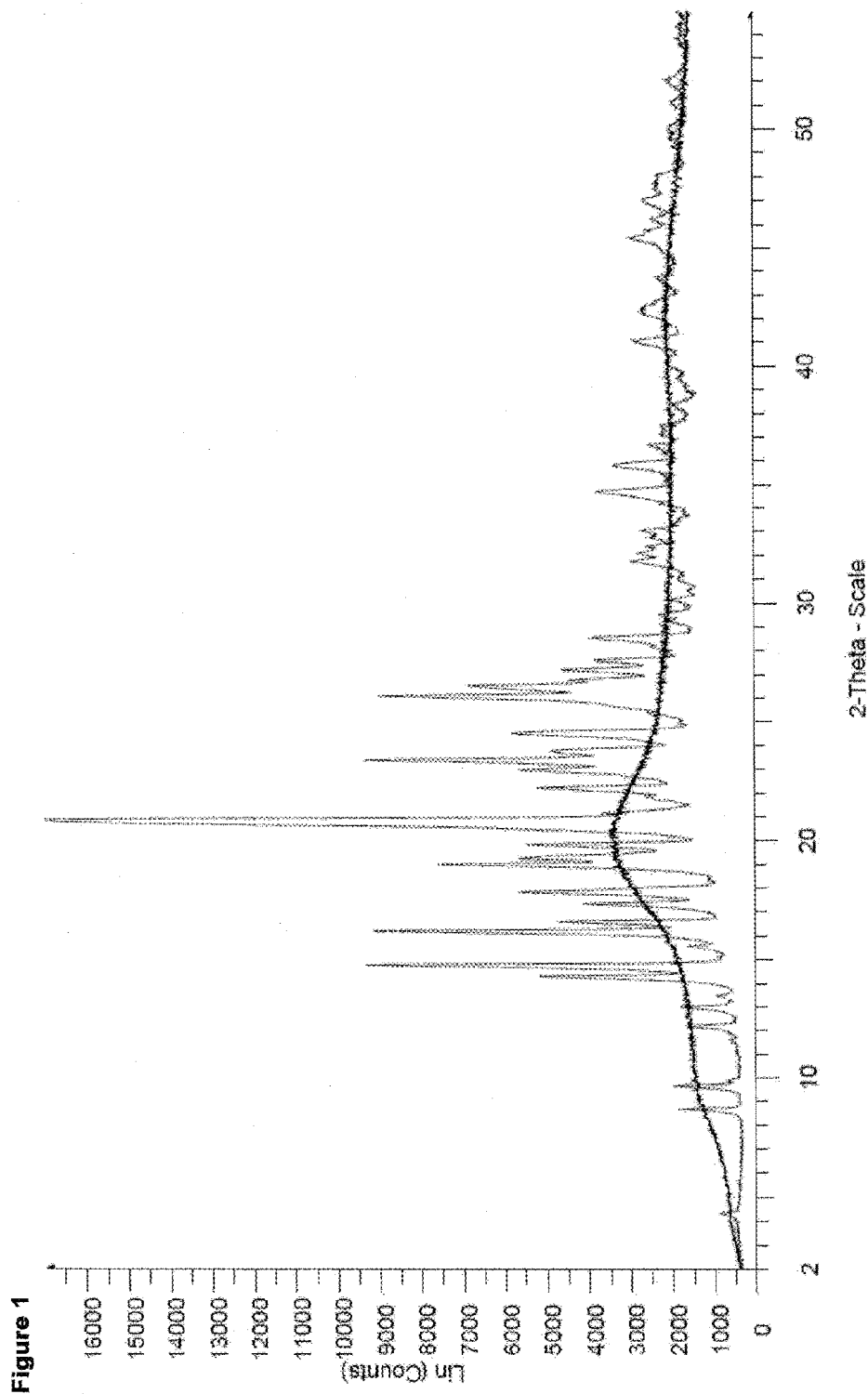
FIG. 1 shows XRD patterns of a spray-dried formulation of ivabradine adipate with HPMC Pharmacoat 603 (flat curve) and of crystalline ivabradine adipate (peaks).

Ivabradine adipate is characterized by an XRD pattern having a characteristic peak at 20.6±0.2 degrees 2-theta, in particular having characteristic peaks at 14.6±0.2, 16.0±0.2, 18.8±0.2, 20.6±0.2, 23.2±0.2, 24.3±0.2, 25.9±0.2 and 26.3±0.2 degrees 2-theta, and preferably further at 8.6±0.2, 9.6±0.2, 12.1±0.2 and 12.9±0.2 degrees 2-theta. The XRD pattern of ivabradine adipate is shown in FIG. 1.

Presently, under a homogeneous mixture a solid solution of the active substance in the excipient is understood. So, the solid composition possesses only one phase defined by a glass transition point with the dissolved active substance being present evenly distributed in the excipient. So, the homogeneous mixture contains at least substantially no phases of pure excipient or pure active substance. Rather, excipient and active substance are mixed on a molecular level so that phase boundaries between excipient and active substance can be observed neither visually nor with other physical methods. Accordingly, the active substance is not present in the crystalline form in the solid composition according to the invention. Rather, the active substance is distributed on a molecular level between the molecules of the excipient. Thus, the active substance can no longer be detected for example by X-ray diffraction powder pattern, but by spectroscopic methods such as for example the confocal Raman spectroscopy. Here, pressed disks are made of the samples on the surface of which a mapping measurement can be performed along a quadratic raster of 15×15 points, spaced by 2 µm in both directions. The measurements are performed with a Senterra Raman microscope (Bruker Optics) at 785 nm (100 mW) using a 50× objective (laser beam diameter approx. 2 µm). If the mutual distribution of the components in the solution is molecularly disperse particles consisting of pure components are not observed, i.e. at all points of the raster area Raman spectra containing signals of all components are measured. The component being present in major amount is referred to as solvent wherein the other component is (really) dissolved.

The molecularly disperse distribution of the active substance in the excipient and thus, the presence of a solution can alternatively be detected for example by electron micrographs or DSC measurements.

Presently, by a solid composition there is meant a composition that is present as dimensionally stable body at a temperature of 23° C. and a pressure of 101 kPa.

Since a complete dissolution of the active substance in the excipient can be sometimes difficult in the preparation of corresponding solid compositions the present invention also comprises solid compositions still containing minor amounts of undissolved active substance particles. Such minor amounts of undissolved particles do not interfere with the advantageous properties of the composition according to the invention. However, there should be present less than 15% by weight, preferably less than 10% by weight, more preferred less than 5% by weight and particularly preferred less than 1% by weight of the total amount of the active substance in the form of particles in the solid composition. Especially preferred is that the composition according to the invention does not contain any active substance particles, in particular no active substance particles that can be visually observed for example under a light microscope due to the phase boundaries occurring between the active substance and the excipient. The solid composition according to the invention therefore should show a complete homogeneous image on visual inspection in which no phase boundaries can be seen.

By the solid composition according to the invention the active substance is evenly distributed in the excipient and thus "pre-diluted". The thus obtained composition can be easily processed into pharmaceutical products either directly or for example with further excipients. In particular, the composition according to the invention permits uniform mixing with further excipients without the risk of separation. Moreover, by pre-diluting the active substance homogeneous distribution in pharmaceutical formulations made thereof and thus, uniformity of the content of the active substance of said formulations are ensured. A further advantage of the composition according to the invention is that the molecularly disperse distribution of the active substance in the excipient accelerates the dissolution of the active substance. For example, this can be of significance if an ivabradine salt is used that is sparingly soluble or at least less soluble in water.

The amount of the active substance in the solid composition according to the invention is not particularly limited. On the one hand, it rather depends on the desired dilution effect and on the other hand on the solubility of the active substance in the selected excipient. For example, the weight ratio of active substance, based on the free base, to excipient may be in the range of 1:1 to 1:1,000. Preferred ranges are for example 1:1 to 1:500, 1:1 to 1:100, 1:10 to 1:50, and in particular about 1:50. All of the above-mentioned upper and lower limits can also be combined with each other in order to form additional preferred ranges.

As the excipient any pharmaceutically acceptable excipient can be selected that is capable of forming a homogeneous molecularly disperse mixture with ivabradine or the selected pharmaceutically acceptable salt thereof. Thus, the excipient must be able to dissolve the active substance in the desired concentration. Suitable excipients are for example polymers, copolymers, saccharides, oligosaccharides, polysaccharides, sugar alcohols, lipids, and waxes. The excipient should have a melting point of greater than 50° C. and/or a glass transition temperature Tg of greater than 15° C.

In one embodiment of the present invention the employed excipient is a polymer that has a glass transition temperature (Tg) of >15° C., preferably 20° C. to 150° C., and in particular 25° C. to 100° C. Here, the glass transition temperature is that temperature at which the amorphous or partly crystalline polymer changes from the solid to the liquid state. Here, a significant change of physical parameters such as hardness and elasticity occurs. Typically, below the glass transition temperature a polymer is glassy and hard, above the glass transition temperature it changes into a rubber-like to viscous state. The determination of the glass transition temperature takes place in the context of this invention by means of differential scanning calorimetry (DSC). For that, for example a device of Mettler Toledo DSC 1 can be used. It works with a heating rate of 10° C. and a cooling rate of 50° C.

The polymer used as the excipient preferably has an average molecular weight of 1,000 to 250,000 g/mol, more preferred of 2,000 to 100,000 g/mol, and in particular between 4,000 and 50,000 g/mol. Additionally, the polymer used should have a viscosity of 2 to 8 mPa/s in a 2% by weight solution in water, each measured at 25° C. according to the European Pharmacopoeia (Ph. Eur.), $6^{th}$ edition, section 2.2.10.

In a further preferred embodiment the polymer has a water solubility of >0.01 mg/ml at 23° C.

Preferably, there can be employed hydrophilic polymers as the excipient. This refers to polymers having hydrophilic groups, for example hydroxy, amino, ester, ether, alkoxy, acrylate, methacrylate, sulfonate, carboxylate, and quarternary ammonium groups. Hydroxy groups are preferred.

According to the invention the polymer used as the excipient can be selected from the group consisting of cellulose derivatives, such as hydroxypropylmethylcellulose (HPMC), carboxymethylcellulose (CMC), ethylcellulose, methylcellulose, hydroxyethylcellulose, ethylhydroxyethylcellulose, and hydroxypropylcellulose (HPC), micro-crystalline cellulose, starch, arabic gum, tragacanth gum, guar gum, alginic acid, alginates, polyvinylpyrrolidone (PVP), polyvinylacetates (PVAC), polyvinyl alcohols (PVA), polyvinyl alcohol derivatives, polymers of the acrylic acid and its salts, polyacrylamides, polymethacrylates, polymethacrylate derivatives, vinylpyrrolidone vinylacetate copolymers (e.g., Soluton), polyalkylene glycoles, such as poly(propylene glycol) and polyethylene glycol and its derivatives such as polyethylene glycol glycerides and fatty acid esters of polyethylene glycol, co-blockpolymers of the polyethylene glycol, in particular co-blockpolymers of polyethylene glycol and poly(propylene glycol), co-blockpolymers of ethylene oxide and propylene oxide (Poloxamer, Pluronic), sucrose fatty acid esters as well as mixtures of two or more of the mentioned polymers.

Examples of suitable sugar alcohols are lactose, mannitol, sorbitol, xylitol, isomalt, glucose, fructose, maltose, arabinose, and mixtures of two or more of the mentioned compounds.

Further, gelatin and phospholipides are suitable excipients.

The following excipients have been found to be particularly suitable: sucrose, sorbitol, xylitol, eudragite, polyethylene glycol (PEG, for example PEG 4000 or PEG 20000), polyoxyethylene glycol monostearate, glycerol polyethylene glycol ricinolate, macrogol glycerol stearate (e.g. Gelucire), glycerol palmitol stearate (e.g., Precirol), macrogol glycerol laurate (e.g., Gelucire 50), polyethylene glycol cetylstearyl ether (e.g., Cremophor A25), glycerol monostearate (e.g., lmwitor), polyvinylpyrrolidone (PVP, for example PVP 30 or Povidon VA64), methacrylates, cellulosederivatives such as celluloseethers (for example Methocel K4M CR Premium), methylcellulose (MC), hydroxypropylcellulose (HPC, for example HPC HF), and hydroxypropylmethylcellulose (HPMC, for example HPMC 615), and copolymers of polyvinyl alcohol or polyvinylpyrrolidone such as Copovidone (of vinylacetate and vinylpyrrolidone, e.g., Kollidon VA64) or Pluronic, e.g., Pluronic F68, a block-copolymer of ethylene oxide and propylene oxide. Polyvinylpyrrolidone and block-copolymers of ethylene oxide and propylene oxide are particularly preferred.

All the above-mentioned excipients can be employed alone or as mixture of two or more of the mentioned compounds.

The solid compositions according to the invention can be prepared by mixing excipient and active substance such that a homogeneous, molecularly disperse mixture is obtained. For example, an appropriate mixing can be done in combined melt of excipient and active substance preferably by melt extrusion with care being taken that the extrusion conditions are selected such that not only the excipient is molten but a melt of active substance and excipient forms so that the active substance may distribute molecularly disperse in the excipient melt.

Alternatively, it is possible to carry out the mixing by dissolving the excipient and the active substance in a solvent and to subsequently evaporate the solvent. When evaporating the solvent care must be taken that the excipient and the active substance do not precipitate next to each other but form the desired homogeneous, molecularly disperse mixture.

As the solvent any solvent can be employed that is able to dissolve both the excipient and the active substance. For example, water or a mixture of water and ethanol, for example an aqueous ethanol solution of about 20% to 30% by volume, are suitable.

Alternatively it is possible to spray the solution for example onto inert excipient particles, so-called nonpareils. Spraying on can be done for example in a fluid-bed granulator. By spraying onto the excipient particles the excipient and the active substance together separate from the solution as a homogeneous, molecularly disperse mixture.

The solid composition according to the invention can be further processed to a pharmaceutical product, in particular a solid pharmaceutical dosage form according to methods that are common and known to the skilled person. Preferably, this is a capsule, a tablet, a tablet disintegrating in the mouth, a retarded release tablet, pellets, or granules. Preferred are tablets that can be prepared by direct compressing with excipients that are conventionally used for that.

Additionally, the pharmaceutical product can contain one or more further pharmaceutically acceptable excipients, such as e.g. fillers, glidants, flow regulators, release agents, and disintegrants. ("Lexikon der Hilfsstoffe für Pharmazie, Kosmetik and angrenzende Gebiete", edited by H. P. Fiedler, 4$^{th}$ Edition, and "Handbook of Pharmaceutical Excipients", 3$^{rd}$ Edition, edited by Arthur H. Kibbe, American Pharmaceutical Association, Washington, USA, and Pharmaceutical Press, London).

Fillers: The pharmaceutical composition can contain one or more filler(s). In general, a filler is a substance that increases the bulk volume of the mixture and thus the size of the resulting pharmaceutical dosage form. Preferred examples of fillers are lactose and calcium hydrogenphosphate. The filler may be present in a proportion of 0 to 99% by weight, preferred between 10 and 85% by weight of the total weight of the composition.

Glidants: The function of the glidant is to ensure that the pelletizing and the ejection take place without much friction between the solids and the walls. Preferably, the glidant is an alkaline-earth metal stearate or a fatty acid, such as stearic acid. Typically, the glidant is present in an amount of 0 to 2% by weight, preferably between 0.5 and 1.5% by weight of the total weight of the pharmaceutical composition.

Disintegrants: Usually, by a disintegrant is meant a substance that is capable of breaking up the tablet into smaller pieces as soon as it is in contact with a liquid. Preferred disintegrants are croscarmellose sodium, sodium carboxymethyl starch, cross-linked polyvinylpyrrolidone (crospovidon), sodium carboxymethyl glycolate (e.g. explotab) and sodium bicarbonate. Typically, the disintegrant is present in an amount of 0 to 20% by weight, preferably between 1 and 15% by weight of the total weight of the composition.

Flow regulators: As the flow regulator there can be used e.g. colloidal silica. Preferably the flow regulator is present in an amount of 0 to 8% by weight, more preferably in an amount between 0.1 and 3% by weight of the total weight of the composition.

Release agents: The release agent can be e.g. talcum and is present in an amount between 0 and 5% by weight, preferably in an amount between 0.5 and 3% by the weight of the composition.

Normally, the solid composition according to the invention and the pharmaceutical product according to the invention have a uniformity of the active substance content (content uniformity) of 95% to 105%, preferably 98% to 102%, in particular 99% to 101% of the average content. That is, all dosage forms, for example tablets, have a content of active substance between 95% and 105%, preferably between 98% and 102%, in particular between 99% and 101% of the average active substance content. The "content uniformity" is determined according to Ph. Eur. 6.0, section 2.9.6.

Preferably, the pharmaceutical composition according to the invention is present as tablet containing ivabradine preferably in an amount of 1 mg to 20 mg, more preferred of 3 mg to 15 mg, in particular of 5 mg to 10 mg. Thus, object of the invention are in particular tablets containing 5 mg or 7.5 mg ivabradine.

Preferably, the pharmaceutical composition according to the invention is administered twice a day.

In a preferred embodiment, the oral administration of the formulation according to the invention to a human as a patient leads to a plasma level profile which is distinguished by a $c_{max}$ (maximum plasma level) based on a twice daily intake of 5 mg of the active substance ivabradine, in the steady state, of about 5 to 40 ng/ml, preferably 10 to 30 ng/ml.

The abovementioned values for the plasma level are preferably mean values, obtained by investigations of blood samples of a group of 10 test subjects (having an average body weight of 70 kg), the corresponding blood samples having been taken 0, 1, 2, 4, 6, 8, 12, 24 and 48 hours after oral administration of the composition according to the invention in the steady state. The determination of the plasma level values can preferably be carried out by suitable HPLC-MSMS methods.

XRD samples were analysed on a Bruker-AXS D8 Advance powder X-Ray diffractometer. The measurement conditions were as follows:

Measurement in Bragg-Brentano-Geometry on vertical goniometer (reflection, theta/theta, 435 mm measurement circle diameter) with sample rotation (30 rpm) on 9 position sample stage

| | |
|---|---|
| Radiation: | Cu Kα1(1.5406 Å), Tube (Siemens FLCu2K), power 40 kV/40 mA |
| Detector: | position sensitive detector VANTEC-1 3° capture angle (2theta), Anti scatter slit 6.17 mm Detector slit 10.39 mm 4° soller slit, primary beam stop (<2° 2theta) |
| Monochromator: | None |
| Second β filter: | Ni filter 0.1 mm (0.5%) |
| Start angle: | 2° |
| End Angle: | 55° |
| Measurement time: | 11 min |
| Step: | 0.016° 2Theta |
| Software: | EVA (Bruker-AXS, Karlsruhe). |

Now, the present invention is explained in more detail with respect to the following examples without these should be interpreted as being restrictive.

EXAMPLES

Example 1

Preparation of a Solid Solution by Melt Extrusion

| | |
|---|---|
| Ivabradine | 5 mg |
| Pluronic | 50 mg |
| Avicel | 60 mg |
| Sodium Carboxymethyl Starch | 15 mg |
| Colloidal Silica | 4 mg |
| Magnesium Stearate | 2 mg |

The active substance was mixed with Pluronic and extruded in a EuroLab Twin Screw Extruder Leistritz micro 18. Here, the process parameters are to be controlled such that a too strong degradation tendency by working at the melting point of ivabradine is avoided.

After cooling down and sieving through a 700 μm sieve the additional excipients except for magnesium stearate were added and mixed for 15 minutes in a tumbling mixer (Turbula T10B). Magnesium stearate was sieved into the mixture through a 500 μm sieve and subsequently the mixture was mixed for another 3 minutes in the tumbling mixer. The finished mixture was compressed on a Korsch excenter press into tablets.

Example 2

Preparation of a Solid Solution by Spray Drying

| Ivabradine | 5 mg |
| Povidon VA 64 | 50 mg |
| Lactose Monohydrate | 70 mg |
| Sodium Carboxymethylcellulose | 13 mg |
| Colloidal Silica | 4 mg |
| Magnesium Stearate | 2 mg |

The active substance together with Povidon VA 64 was dissolved in a suitable solvent. Then, it was sprayed on a Büchi spray tower at the following parameters:

Spraying Pressure: 3-4 bar

Nozzle: 1.4 mm

Aspirator: 90%

After sieving through a 700 μm sieve the additional excipients except for magnesium stearate were added and mixed for 15 minutes in a tumbling mixer (Turbula T10B). Magnesium stearate was sieved into the mixture through a 500 μm sieve and subsequently the mixture was mixed for another 3 minutes in the tumbling mixer. The finished mixture was compressed on a Korsch excenter press into tablets.

An advantage of the spray drying method is that the selection of the polymer can be done independently from its melting point.

Example 3

Preparation of a Solid Solution by Melt Extrusion

| Ivabradine | 6.51 mg |
| Pluronic | 50.00 mg |
| Avicel PH101 | 25.00 mg |
| Sodium Carboxymethyl Starch | 14.91 mg |
| Colloidal Silica | 2.58 mg |
| Magnesium Stearate | 1.00 mg |

The active substance was mixed with Pluronic and extruded in a EuroLab Twin Screw Extruder Leistritz micro 18. Here, the process parameters are to be controlled such that a too strong degradation tendency is avoided by working at the melting point of ivabradine adipate.

After cooling down and sieving through a 700 μm sieve the additional excipients except for magnesium stearate were added and mixed for 15 minutes in a tumbling mixer (Turbula T10B). Magnesium stearate was sieved into the mixture through a 500 μm sieve and subsequently the mixture was mixed for another 3 minutes in the tumbling mixer. The finished mixture was compressed on a rotary press (Riva Piccola) into tablets.

Figure 2:
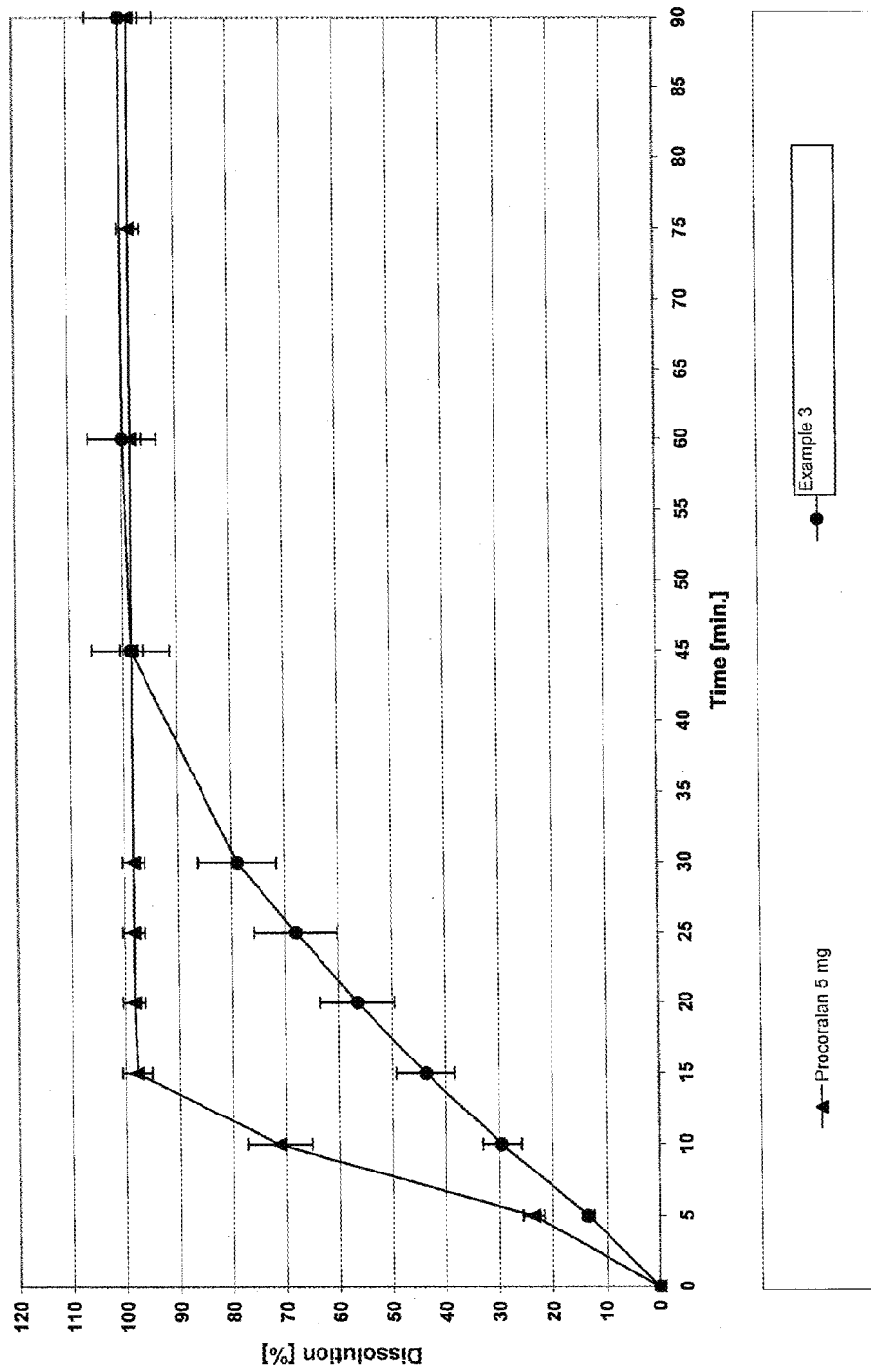
FIGS. 2 to 5 show dissolution profiles of the tablets of examples 3 to 6, respectively.

The tablets obtained in Example 1 show a dissolution profile (conditions: 500 mL 0.1 n HCl pH 1.7, 37° C., 50 rpm basket (USP app. I)) as shown in FIG. 2.

Example 4

Preparation of a Solid Solution by Spray Drying

| Ivabrading adipate | 6.56 mg |
| HPMC | 50.00 mg |
| Calcium Hydrogenphosphate | 26.94 mg |
| Sodium Carboxymethylcellulose | 13.00 mg |
| Colloidal Silica | 2.50 mg |
| Magnesium Stearate | 1.00 mg |

The active substance together with HPMC was dissolved in suitable solvent, e.g. water. Then, it was sprayed on a Büchi spray tower at the following parameters:

Spraying Pressure: 3-4 bar

Nozzle: 1.4 mm

Aspirator: 90%

After sieving through a 700 μm sieve the additional excipients except for magnesium stearate were added and mixed for 15 minutes in a tumbling mixer (Turbula T10B). Magnesium stearate was sieved into the mixture through a 500 μm sieve and subsequently the mixture was mixed for another 3 minutes in the tumbling mixer. The finished mixture was compressed on a rotary press (Riva Piccola) into tablets.

An advantage of the spray drying method is that the selection of the polymer can be done independently from its melting point.

Figure 3:
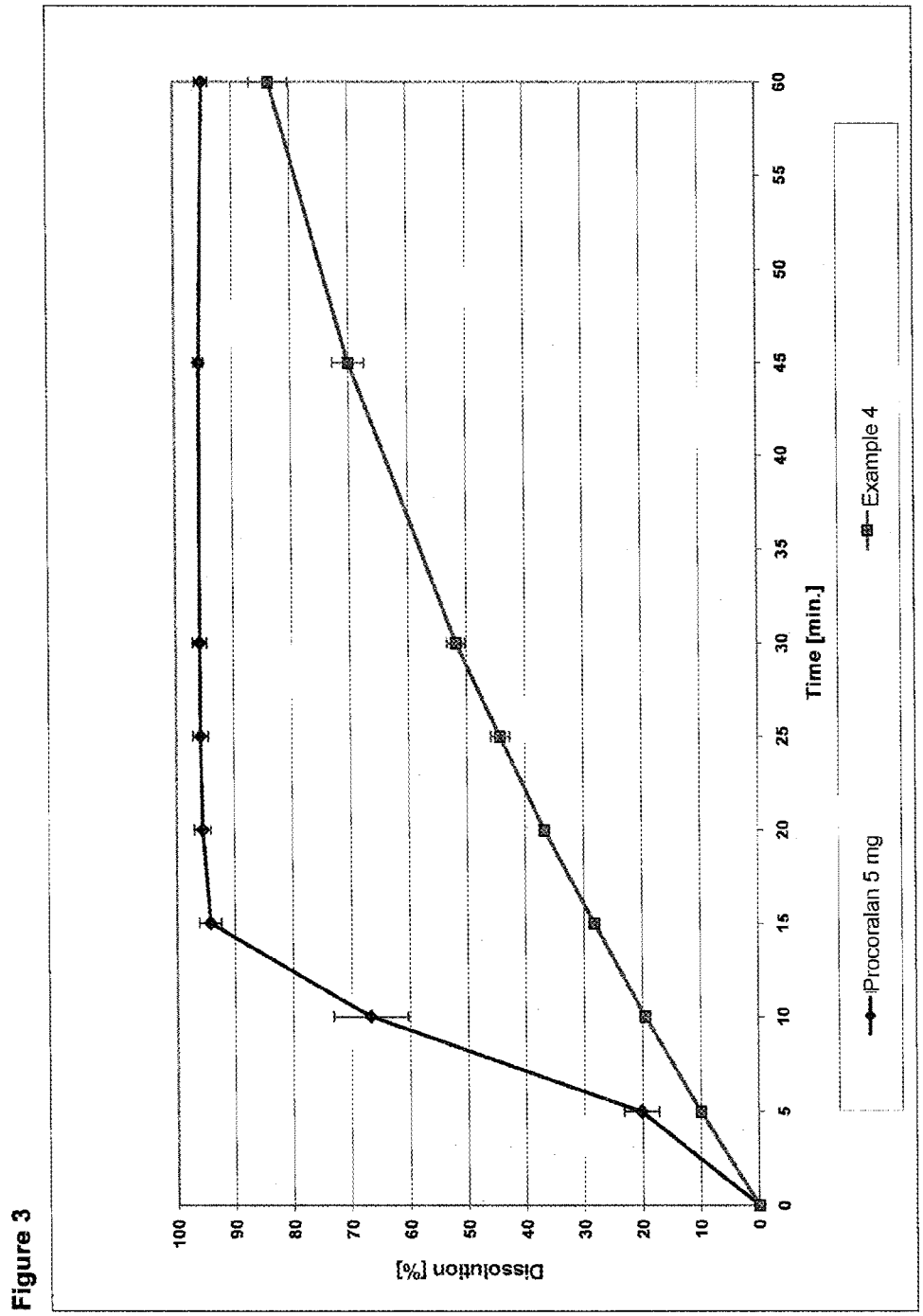

The dissolution profile of the tablets obtained according to Example 4 is shown in FIG. 3 (conditions: 500 mL 0.1 N HCl pH 1.2, 37° C., 50 rpm, paddle (USP app. II)).

Example 5

Preparation of a Solid Solution by Melt Extrusion

| Ivabradine HCl form I | 5.42 mg |
| Pluronic | 50.00 mg |
| Avicel PH101 | 25.00 mg |
| Sodium Carboxymethyl Starch | 15.00 mg |
| Colloidal Silica | 2.58 mg |
| Magnesium Stearate | 2.00 mg |

The active substance was mixed with Pluronic and extruded in a EuroLab Twin Screw Extruder Leistritz micro 18. Here, the process parameters are to be controlled such that a too strong degradation tendency by working at the melting point of ivabradine is avoided.

After cooling down and sieving through a 700 μm sieve the additional excipients except for magnesium stearate were added and mixed for 15 minutes in a tumbling mixer (Turbula T10B). Magnesium stearate was sieved into the mixture through a 500 μm sieve and subsequently the mixture was mixed for another 3 minutes in the tumbling mixer. The finished mixture was compressed on a rotary press (Riva Piccola) into tablets.

Figure 4:
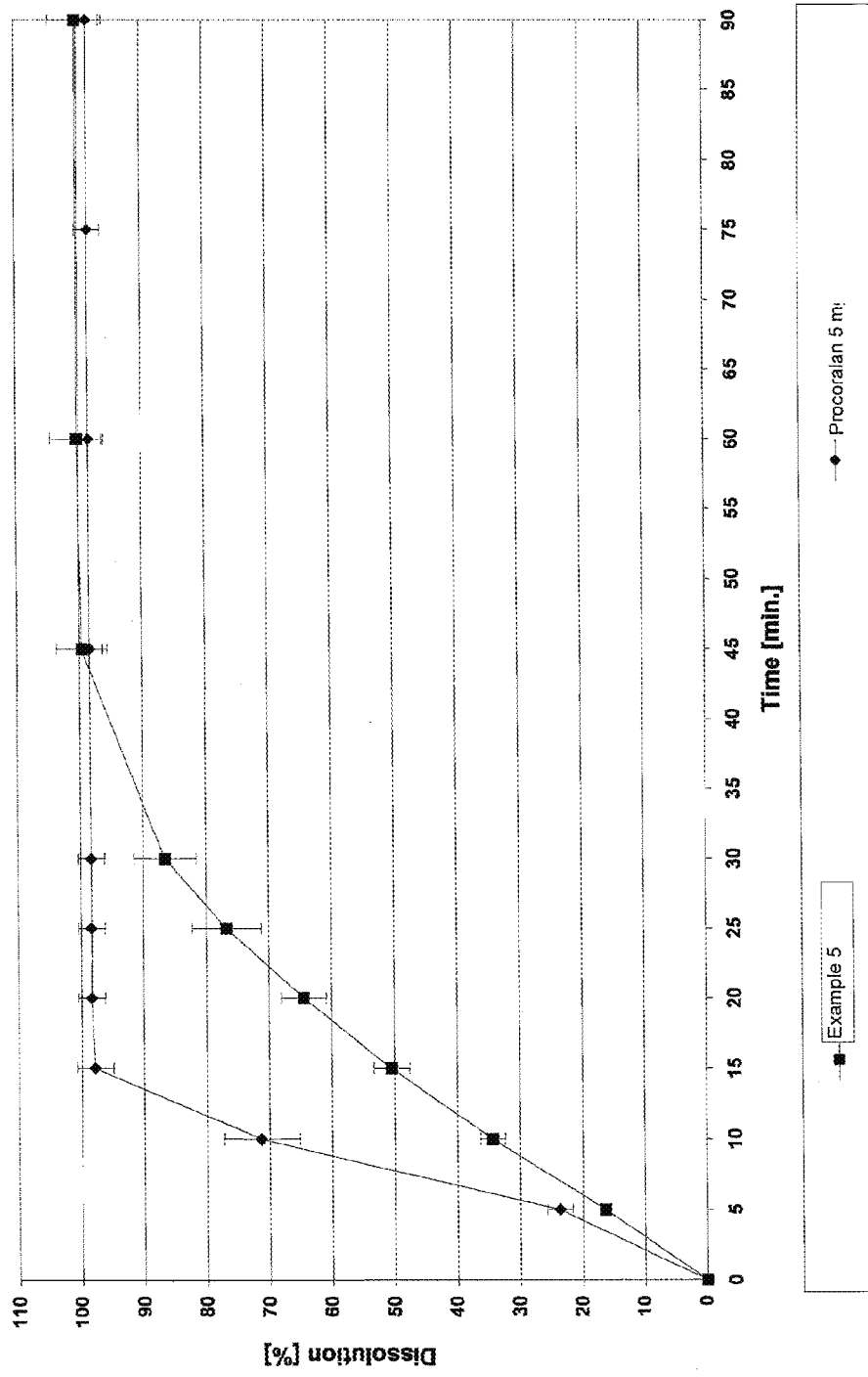

The dissolution profile of the tablets obtained according to Example 5 is shown in FIG. 4 (conditions: 500 mL 0.1 nHCl pH 1.2, 37° C., 50 rpm, basket (USP app. I)).

Example 6

Preparation of a Solid Solution by Melt Extrusion

| | |
|---|---|
| Ivabradine HCl form I | 5.42 mg |
| Povidon VA64 | 50.00 mg |
| Lactose Monohydrate | 25.00 mg |
| Crospovidon | 15.00 mg |
| Colloidal Silica | 2.58 mg |
| Magnesium Stearate | 2.00 mg |

The active substance was mixed with Povidon VA64 and extruded in a EuroLab Twin Screw Extruder Leistritz micro 18. Here, the process parameters are to be controlled such that a too strong degradation tendency by working at the melting point of ivabradine is avoided.

After cooling down and sieving through a 700 μm sieve the additional excipients except for magnesium stearate were added and mixed for 15 minutes in a tumbling mixer (Turbula T10B). Magnesium stearate was sieved into the mixture through a 500 μm sieve and subsequently the mixture was mixed for another 3 minutes in the tumbling mixer. The finished mixture was compressed on a rotary press (Riva Piccola) into tablets.

Figure 5:
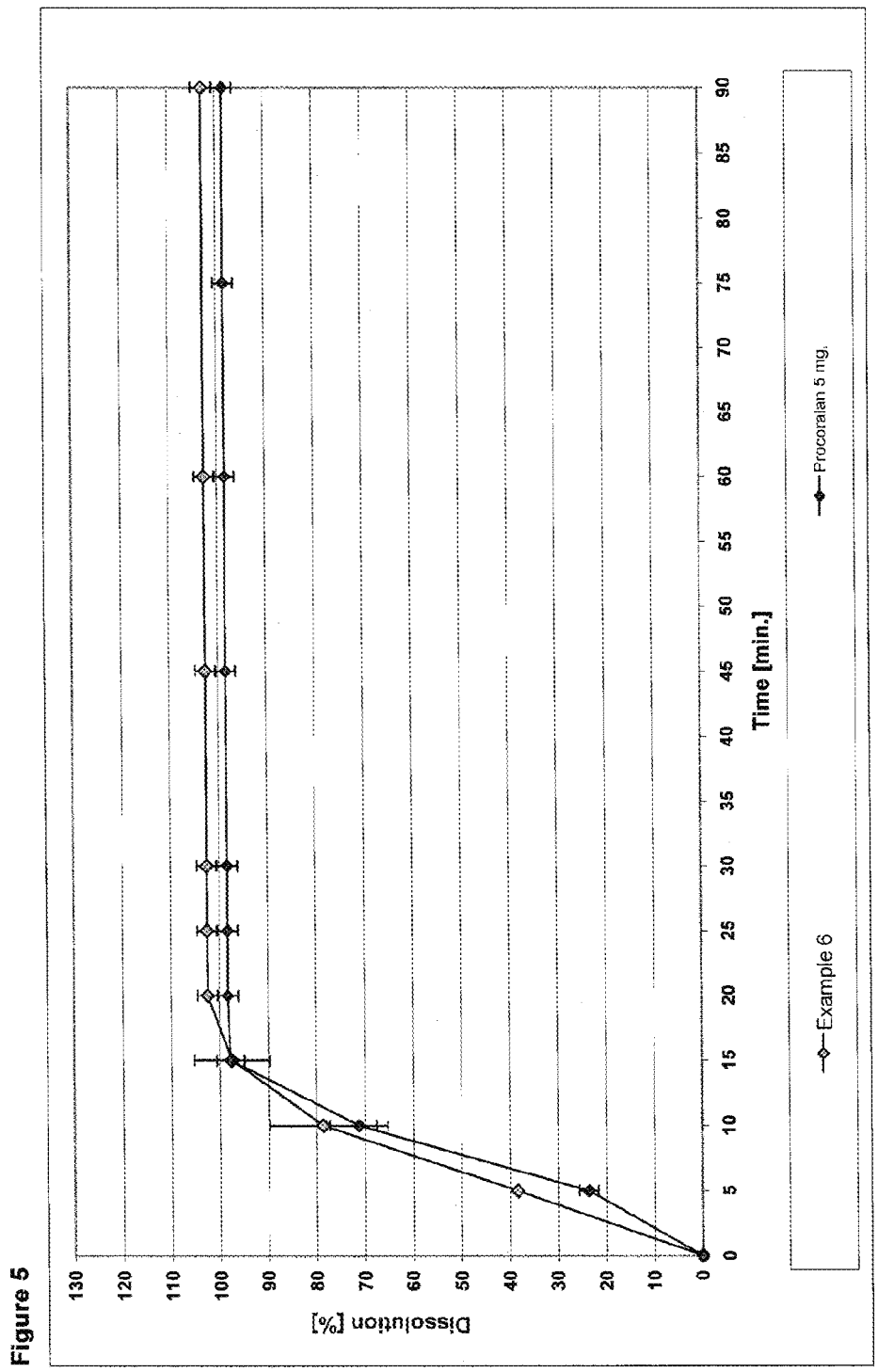

The dissolution profile of the tablets obtained according to Example 6 is shown in FIG. 5 (conditions: 500 mL 0.1 n HCl pH 1.2, 37° C., 50 rpm, basket (USP app. I)).

Example 7

Preparation of a Solid Solution by Spray Drying

A solid solution of ivabradine adipate and hydroxypropyl methyl cellulose (Pharmacoat 603) was prepared by spray drying.

XRD patterns were measured of the formulation and of crystalline ivabradine adipate, which were shown in FIG. 1. The flat curve is obtained from the solid solution. This indicates that no crystalline active substance is present in the formulation. The XRD pattern of crystalline ivabradine adipate shows peaks instead.

Raman spectra were measured on a Senterra Raman microscope (Bruker Optics) at 785 nm (100 mW) using a 50× objective (laser beam diameter approx. 2 μm) and a pinhole type aperture (50 μm) in low resolution mode on a quadratic raster of 15×15 points, spaced by 2 μm in both directions. The OPUS software (version 6) was used for measurement and processing of the spectra.

The Raman spectrum of the formulation is dominated by the excipient Pharmacoat 603. However, two adjacent signals of Ivabradine adipate (1607 and 1592 $cm^{-1}$) can be clearly recognized in a region which is not obscured by excipient signals. For visualization of the Ivabradine adipate content these signals have to be put in relation to a signal of the excipient. A clear signal of the latter, which is free from Ivabradine adipate, cannot be found. Therefore, a region containing signals of both Ivabradine adipate and excipient is chosen for this purpose. Integration area 1, which refers to Ivabradine adipate only, ranges from 1625 to 1569 $cm^{-1}$, while integration area 2, which ranges from 1502 to 1416 $cm^{-1}$, covers both Ivabradine adipate and the excipient. For pure Ivabradine adipate, the integral 1/integral 2-ratio is 0.417. For a solid solution containing Ivabradine adipate and an excipient, which contributes to the intensity of integral 2 only, a value below 0.417 is expected. The experimentally observed distribution of Ivabradine adipate within the formulation appears quite even: the smallest and largest values of the integral 1/integral 2-ratio are 0.058 and 0.108, the mean value is 0.083 with a standard deviation of 0.008.

Figure 6:
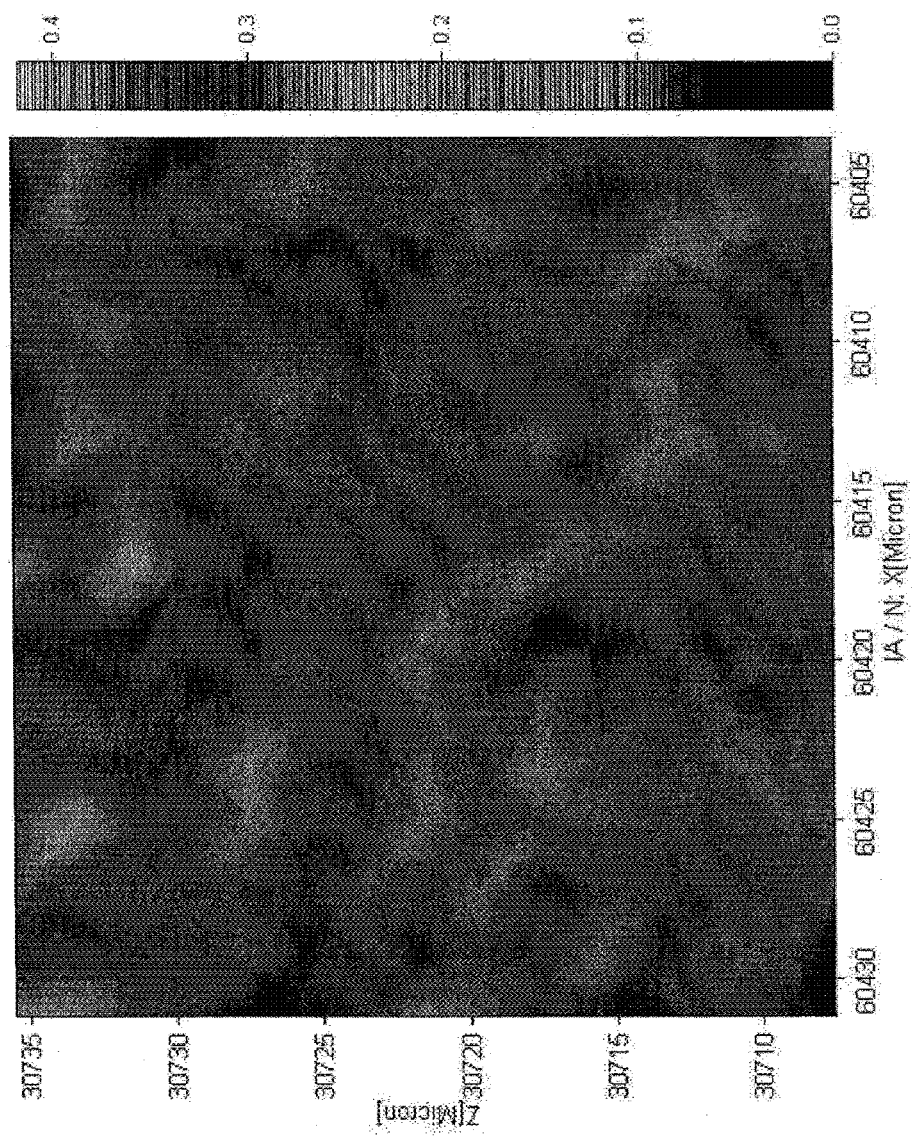
FIG. 6 shows a Raman spectrum of a formulation of ivabradine adipate with HPMC Pharmacoat 603.

A color coded map of integral 1/integral 2-ratio over the measured area is shown in FIG. 6, where the color ranges from 0 to the maximum possible value of 0.417. It is evident that at all points of the sample the integral ratio is inside a range of approximately 0.006 to 0.11, i.e. the value for pure ivabradine adipate particles is by far not reached.

The invention claimed is:

1. A solid composition containing ivabradine or a pharmaceutically acceptable salt thereof as active substance in combination with at least one pharmaceutically acceptable excipient characterized in that the excipient and the active substance are present in the form of a solid solution, wherein the pharmaceutically acceptable excipient is selected from the group consisting of sucrose, sorbitol, xylitol, polyethylene glycol, polyoxyethylene glycol monostearate, glycerol polyethylene glycol ricinolate, macrogol glycerol stearate, glycerol palmitol stearate, macrogol glycerol laurate, polyethylene glycol cetylstearyl ether, glycerol monostearate, polyvinylpyrrolidone, hydroxypropylmethylcellulose (HPMC), carboxymethylcellulose (CMC), ethylcellulose, methylcellulose (MC), hydroxyethylcellulose, ethylhydroxyethylcellulose, hydroxypropylcellulose (HPC), micro-crystalline cellulose, cellulose ethers, copovidone, and ethylene oxide-propylene oxide block-copolymers.

2. The solid composition according to claim 1, wherein less than 15% by weight, of the active substance, based on its total amount, is present in the form of particles.

3. The solid composition according to claim 1, wherein less than 5% by weight of the active substance, based on its total amount, is present in the form of particles.

4. A method for the preparation of a solid composition according to claim 1, said method comprising the step of mixing of excipient and active substance to form a solid solution comprising a homogeneous, molecularly disperse mixture.

5. The method according to claim 4, wherein mixing is done in a combined melt of excipient and active substance.

6. The method according to claim 4, wherein mixing is done by melt extrusion.

7. The method according to claim 4, wherein mixing is done by dissolving excipient and active substance in a solvent and subsequently evaporating the solvent.

8. A solid composition obtained in accordance to a method of claim 4.

9. A pharmaceutical product containing a composition according to claim 1.

10. The pharmaceutical product according to claim 9, wherein said product is selected from the group consisting of capsules, tablets, tablets that disintegrate in the mouth, retarded release tablets, pellets, and granules.

11. A pharmaceutical product containing a composition according to claim 8.

12. The pharmaceutical product according to claim 11, wherein said product is selected from the group consisting of capsules, tablets, tablets that disintegrate in the mouth, retarded release tablets, pellets, and granules.

* * * * *